United States Patent [19]

Lantero, Jr.

[11] 4,438,196
[45] Mar. 20, 1984

[54] IMMOBILIZATION OF BIOCATALYSTS ON GRANULAR CARBON

[75] Inventor: Oreste J. Lantero, Jr., Goshen, Ind.

[73] Assignee: Miles Laboratories, Inc., Elkhart, Ind.

[21] Appl. No.: 425,942

[22] Filed: Sep. 28, 1982

[51] Int. Cl.$^3$ .................... C12P 19/20; C12N 11/02; C12N 11/08; C12N 11/06

[52] U.S. Cl. .................................. 435/96; 435/177; 435/180; 435/181

[58] Field of Search ............... 435/174, 177, 176, 180, 435/181, 95, 96, 98, 99

[56] References Cited

U.S. PATENT DOCUMENTS

| | | | |
|---|---|---|---|
| 3,796,634 | 3/1974 | Haynes et al. | 435/176 X |
| 4,141,857 | 2/1979 | Levy et al. | 435/181 |
| 4,289,853 | 9/1981 | Bailey et al. | 435/177 |
| 4,337,313 | 6/1982 | Hershberger et al. | 435/181 X |

OTHER PUBLICATIONS

Liu, et al., *Biotechnol. Bioeng.* 17, 1695–1696, (1975).
Cho, et al., *Biotechnol. Bioeng,* 20, 1651–1665, (1978).

*Primary Examiner*—David M. Naff
*Attorney, Agent, or Firm*—Jerome L. Jeffers

[57] ABSTRACT

Disclosed is a process whereby enzymes are immobilized on activated granular carbon. The process involves treating the carbon with a polyamine compound having pendant amino groups to cause the polyamine to adhere to the carbon leaving pendant amine groups free to further react. The free amine groups are derivatized by treatment with a difunctional compound having amine reactive moieties, so that free amine groups of the enzyme can be covalently bound to the polyamine via the amine reactive compound. By this method, enzymes can be immobilized onto granular carbon which provides a support having excellent physical properties.

18 Claims, No Drawings

IMMOBILIZATION OF BIOCATALYSTS ON GRANULAR CARBON

BACKGROUND OF THE INVENTION

This invention involves an immobilized enzyme conjugate and a method of preparing such an immobilized enzyme conjugate. It is known that enzymes, which are proteinaceous in nature and which are commonly water soluble, act as biocatalysts which serve to regulate many and varied chemical reactions which occur in living organisms. The enzymes may also be isolated and used in analytical, medical and industrial applications. For example, they find use in industrial applications in the preparation of food such as cheese or bread as well as being used in the preparation of alcoholic beverages. The enzyme glucose isomerase is extensively used to convert glucose to fructose in the manufacture of high fructose corn syrup.

Since enzymes are commonly water soluble as well as being generally unstable and, therefore, subject to deactivation, they are difficult to remove for reuse from solutions in which they are utilized and they may not retain their catalytic activity over extended periods of time. These difficulties lead to an increased cost in the use of enzymes in commercial scale operations due to the necessity for frequent replacement of the enzyme. In order to reduce the high cost of enzyme replacement, various methods to immobilize or insolubilize enzymes prior to their use have been devised. This immobilization of the enzyme permits its reuse whereas it might otherwise undergo deactivation or be lost in the reaction medium in which it is used. These immobilized enzyme systems may be employed in various reactor systems, for example, in packed columns and stirred tank reactors, depending on the nature of the substrate which is being biochemically reacted.

Several general methods as well as many modifications thereof have been described by which the immobilization of enzymes can be effected.

In U.S. Pat. No. 3,796,634 there is disclosed an immobilization method which involves absorbing a polyamine onto the surface of colloidal sized particles, cross-linking the polyamine with a conventional amine-reactive cross-linking agent, e.g. glutaraldehyde, treating the resulting reaction product with $NaBH_4$ to reduce the aldehyde groups and thereby prevent any covalent bonding between the aldehyde groups and the enzyme's amino group, and absorbing the enzyme onto the treated surface of the particle at a pH such that the colloidal absorbant bears a net electric charge opposite that of the enzyme molecules so that ionic bonding aids other non-covalent bonding forces. This patent describes the absorbant particles as ranging in size from about 50 to about 20,000 angstroms, preferably from about 100 to 200 angstroms in diameter, with the absorbant material being activated charcoal, hydroxyapatite, alumina C gamma, and betonite. This system depends on charge interactions for binding the enzyme to the treated particles. This type of bonding is less desirable than the formation of covalent linkages because ionic interactions are susceptible to the environmental conditions relative to this type of linkage such as pH, ionic strength and temperature.

Liu, et al disclose an immobilization method for lactase on granular carbon in *Biotechnol. Bioeng.* 17, 1695–1696, 1975 which involves absorbing p-aminophenol or 1-phenol-2-amino-4-sulfonic acid to the carbon. These absorbed compounds provide the amino groups with which glutaraldehyde reacts and in turn binds the enzyme. The amino group containing compounds mentioned are monomers which possess different chemical and physical properties than those of a polyamine such as polyethylenimine.

Another group of workers (Cho, et al, Immobilization of Enzymes on Activated Carbon: Properties of Immobilized Glucoamylase, Glucose Oxidase and Gluconolactonase, *Biotechnol. Bioeng.* 20, 1651–1665, 1978) have also immobilized enzymes on granular carbon by covalent attachment. In this process carbon is activated by a carbodiimide which then enables the enzyme to displace the carbodiimide and form an enzyme-carbon complex.

U.S. Pat. No. 4,141,857 (issued Feb. 27, 1979) discloses a method for enzyme immobilization which involves treating an inorganic porous support material such as gamma-alumina having pore diameters of from about 100 to about 55,000 angstroms and a surface area of about 100 to 500 $m^2$ per gram with a solution of a water soluble polyamine and contacting the treated support material with a solution of a bifunctional monomeric material, e.g. glutaraldehyde. This treatment leaves the treated support material suitable for reaction with the enzyme so as to form covalent bonds between the enzyme and the pendant aldehyde groups. In example II of this patent there is described the preparation of an immobilized enzyme conjugate by treating porous alumina spheres sequentially with solutions of polyethylenimine, glutaraldehyde and glucoamylase.

The use of activated granular carbon has received little attention as a support for immobilized enzymes in spite of its many attractive properties and reasonable cost. Granular carbon is used industrially for purification of syrups and other food products, pharmaceutical products, organic acids and various other chemicals by continuous column percolation processes.

SUMMARY OF THE INVENTION

The present invention involves a method of preparing an immobilized enzyme conjugate which comprises the steps of:

(a) contacting porous, granular, activated carbon with a solution of a polyamine compound having pendant amine groups to cause the polyamine to attach itself to the carbon both by absorption to its surface and by entrapment in the pores thereof;

(b) removing the water and unattached polyamine from contact with the carbon and contacting it with an aqueous dispersion of an amine reactive material which is a multifunctional aldehyde, a multifunctional organic halide, a multifunctional anhydride, a multifunctional azo compound, a multifunctional isothiocyanate or a multifunctional isocyanate to cause one of the reactive groups to react with the pendant amine groups and leave an amine reactive group available for further reaction;

(c) removing the water and unreacted amine reactive material from contact with the carbon and contacting it with an aqueous solution of the enzyme to cause the amine groups of the enzyme to react with the unreacted aldehyde groups by the formation of covalent bonds therebetween to thereby immobilize the enzyme.

DESCRIPTION OF THE INVENTION

The granular carbon suitable for use in the present invention will typically have a particle size of from 12 to 40 mesh on the U.S. sieve series. Pore dimensions will preferably range in radii from 35 Å to 1000 Å with the granular carbon support material having a surface area of from 200 to 600 m²/gm.

Specific examples of polyamines suitable for use in the present invention include polyethylenediamine, a polyethylenimine such as, for example, polydiethylenetriamine, polytriethylenetetramine, polypentaethylenehexamine or polyhexamethylenediamine. Other suitable polyamines are polymethylenedicyclohexylamine, polymethylenedianiline, polytetraethylenepentamine and polyphenylenedimine. A copolymer of an epihalohydrin and an alkylene polyamine has also been found to be suitable. While the molecular weight of the polyamine is not deemed critical, polymers with a molecular weight range of from 500 to 100,000 are preferred. Those polyamines which are water soluble are applied to the carbon from their aqueous solutions whereas non-water soluble polymers are applied from organic solents such as methyl alcohol, ethyl alcohol, propyl alcohol, isopropyl alcohol, t-butyl alcohol, acetone, methyl ether, ethyl ether, propyl ether, isopropyl ether, toluene, benzene, xylene, hexane, cyclopentane and cyclohexane. Contacting the carbon with the polyamine solution, which will normally be of a concentration of 1 to 100 gm of polymer to liter of solvent, causes the polyamine to become attached to the surface of the carbon particle. While a portion of the polymer would be expected to be absorbed to the surface of the carbon particle, a major portion will be attracted into the pores of the porous support so that the macromolecule projects out from the pore leaving the functional groups (amino groups) available for further reaction. This is in contrast to the method described in previously mentioned U.S. Pat. No. 3,796,634 in which carbon powder is treated with a solution of polyethylenimine to change its surface charge and thereby allow absorption of the enzyme to the modified carrier. This method depends on charge interaction which is much less desirable than the covalent linkages formed in the process of this invention. The treated carbon is removed from contact with the polyamine solution, such as by filtration, and preferably washed with deionized (DI) water to remove any non-adhering polymer.

The polymer treated carbon is next treated with a solution of a multifunctional amine reactive material such as glutaraldehyde; bis-diazobenzidine-2,2'-disulfonic acid; 4,4'-difluoro-3,3'-dinitrodiphenylsulfone; diphenyl-4,4'-dithiocyanate-2,2'-disulfonic acid; 3-methoxydiphenylmethane-4,4'-diisocyanate; toluene-2-isocyanate-4-isothiocyanate; toluene-2,4-diisothiocyanate; diazobenzidine; diazobenzidine-3,3'-dianisidine; N,N'-hexamethylene bisiodoacetamide; hexamethylene diisocyanate; cyanuric chloride and 1,5-difluoro-2,4-dimitrobenzene by contacting it with an aqueous solution of the agent preferably contained from about 1 to 100 gm per liter of the amine reactive agent. After allowing the reaction to proceed for a time sufficient to permit the aldehyde to derivatize the free amine groups, the treated carbon is removed from the aldehyde solution and preferably washed several times with deionized water. As used herein, the term "derivatize" is intended to represent the formation of a reaction product between the amino functional group of the polymeric molecule bond to the carbon and the amine reactive moiety of the amine reactive agents.

Any enzyme containing an amino group capable of reacting with the amine reactive moiety which is attached to the polymeric material entraped and absorbed in the pores of the granular carbon can be immobilized by this method. These enzymes include, for example, trypsin, papain, hexokinase, ficin, bromelin, lactic dehydrogenase, lactase, glucose isomerase, glucoamylase, chymotrypsin, pronase, acylase, invertase, amylase, glucose oxidase, pepsin, rennin and fungal protease. The derivatized carbon is mixed with an aqueous solution of the enzyme. This can be carried out in a batch or a columnar reactor. Removal of the carbon from the enzyme solution with subsequent water washing provides the carbon immobilized enzyme suitable for use in biocatalytic conversions.

One of the unexpected observations of the enzyme immobilization method of this invention is that the granular carbon becomes tougher in the sense that fewer fines are generated by the treated particles than by those which are untreated. This property, which is very important when considering a heterogeneous biocatalyst is illustrated by the following experiment:

Five samples of granular carbon were treated with varying concentrations of polyethylenimine (PEI) of from 0 to 0.5% (w/v in water). After the PEI treatment, the carbon samples were washed and then treated with 1% glutaraldehyde (GA) (w/v water) at pH 9.0 in 0.02 M borate buffer. The samples in the glutaraldehyde solution were placed on a rotary shaker and agitated for 4 hours. The liquid was then decanted from the carbon and the degree of carbon fines in suspension was estimated on a relative scale of 0 to 5. A zero value represented no observed carbon fines whereas a value of 5 represented a suspension of carbon fines which was completely opaque. The following table summarizes the degree of carbon fines generated during the agitation.

| Carbon Fines Generated During Agitation of PEI Treated Granular Carbon In 1% GA Solution | |
|---|---|
| PEI Treatment | Suspended Fines |
| Control, no PEI | 5 |
| 0.015% PEI | 3 |
| 0.05% PEI | 2 |
| 0.15% PEI | 1 |
| 0.5% PEI | 0.5 |

The protective coating or layer that apparently forms on the granular carbon particle is seen to be dependent on the amount of PEI present. Not only does this process fix enzymes to carbon particles, it also strengthens the carbon particle to reduce its degradation.

Another unique feature of this immobilization process is that previously used granular carbon can be reused for immobilization after regeneration by a simple process involving a base-acid wash. This property of the process is significant because it eliminates any disposal problem for the user and provides a potential economic savings as well. This regeneration potential is exemplified by an experiment in which granular carbon having enzyme immobilized to it by the PEI-GA process was dried and regenerated as follows:

1. Slurried 50 ml dry carbon complex in DI water and washed with several volumes of DI water.
2. Decanted the water and added 250 ml of 0.5 N NaOH, mixed several minutes and let stand 1 hour.

3. Decanted the alkaline solution, and washed the carbon with copious quantity of water.
4. After decanting the water, 250 ml of 0.5 N HCl was added, mixed several minutes and then allowed to stand for 1 hour.
5. Decanted acid and washed with copious amounts of water until the pH of the wash water was 3.6.

The carbon regenerated in this manner was then used to immobilize glucoamylase by the PEI-GA method. An activity of 110 units/ml of carbon was obtained which agrees very well with the 130 units/ml obtained by using a fresh quantity of granular carbon for immobilization.

The immobilization procedure produces a linkage between the enzyme and the polymer absorbed to the granular carbon that is unusually stable, and it has been found that the carbon particle does not become coated and fouled by proteins or other substances when a crude solution of liquefied corn starch is passed through a bed of the immobilized enzyme.

The present invention is further illustrated by the following examples in which all mesh sizes are based on the U.S. standard sieve series.

EXAMPLE I

Immobilization of Amyloglucosidase on PEI-Derivatized Granular Carbon

Prior to use for immobilization, the carbon was acid washed as follows:
1. 100 ml of −20+40 mesh activated granular carbon (Darco) was mixed with concentrated hydrochloric acid and allowed to stand at room temperature for several hours. Enough acid was used to completely immerse the carbon.
2. A large quantity of deionized water was then added to the carbon slurry and decanted after the carbon settled.
3. The water wash of step 2 was repeated several times.
4. The carbon was transferred to a glass column (2.6×70 cm) and water was perculated through the bed until the effluent reached pH 3.5.
5. The carbon was then removed from the column and stored in water at room temperature.

Glucoamylase was immobilized at room temperature by the following procedure:
1. 100 ml of a 4% solution of PEI-600 (Dow, polyethylenimine molecular weight range 40,000–60,000) was added to 10 ml of acid washed granular carbon in a 250 ml round bottom flask, and gently stirred for several hours.
2. The polyamine was then decanted and the carbon washed with copious amounts of water.
3. The immobilized amine groups absorbed on the carbon were derivatized with glutaraldehyde by 200 ml of a 1% glutaraldehyde solution adjusted to pH 9.0. The reaction was allowed to continue for 18 hours while maintaining the pH at 9.0.
4. The glutaraldehyde solution was decanted and the carbon washed with water to remove unreacted glutaraldehyde.
5. 100 ml of glucoamylase (AG, 2.5 ml of Diazyme L-100, Miles Laboratories, Inc.) solution adjusted to pH 7.0 with dilute NaOH(2 N) was added to the derivatized carbon. With gentle stirring for several hours, the pH of the reaction mixture was kept at 7.0.
6. The enzyme solution was decanted and the immobilized enzyme was washed with water.

The activity and stability of the immobilized enzyme was determined by assaying it several times in a recirculation differential reactor as described by Ford, et al in *Enzyme Engineering*, Ed. Wingard, Jr., L.B., Pp. 267, John Wiley & Sons, New York (1972). The assay was conducted at 50° C. using as substrate Maltrin-15 [a low DE (15–18) corn starch obtained from Grain Processing Co., Muscatine, Iowa] in 0.02 M acetate buffer at pH 4.2. To carry out the assay, the substrate is placed in a reservoir and the amount of glucose formed is estimated by the Glucostrate Method (General Diagnostics) whereby the initial velocity of glucose formed per minute is determined from regression analysis. A unit of activity represents the amount of enzyme that forms one $\mu$ mole of glucose per minute under the experimental conditions.

The enzyme was assayed 3 consecutive times with fresh substrate and with a buffer (0.02 M acetate, pH 4.2) wash between each assay to determine the stability of the activity. The following results indicate that AG is immobilized on the derivatized carbon and summarizes its activity.

| ACTIVITY OF AG IMMOBILIZED ON CARBON ACTIVITY | | |
|---|---|---|
| Assay | $\mu$ moles G (min./ml/enz.)$^{-1}$ | $\mu$ moles G (min./gm/enz.)$^{-1}$ |
| 1st | 148 | 344 |
| 2nd | 145 | 338 |
| 3rd | 138 | 322 |

EXAMPLE II

Immobilization of Bacterial Alpha-Amylase on PEI Derivatized Carbon

A 5 ml quantity of PEI-glutaraldehyde derivatized granular carbon as in example I was used to immobilize bacterial alpha-amylase (Taka-Therm ®, Miles Laboratories, Inc.). The enzyme solution used for treating the derivatized carbon consisted of 1 ml Taka-Therm ® diluted to 50 ml with water. The immobilization procedure was carried out as described in example I. The resulting immobilized preparation, after being washed with buffer, (0.02 M acetate containing 10 mM CaCl$_2$, pH 6.0) was assayed in the differential reactor using as substrate 4% soluble starch in 0.02 M acetate buffer at pH 6.0 containing 10 mM CaCl$_2$. The degree of starch hydrolysis was determined by measuring the amount of reducing groups formed by the ferricyanide method described by Ghuysen, et al in *Methods in Enzymology*, Vol. VIII, Pp. 685, Academic Press, New York, 1966, in which glucose was used as the reference. The immobilized alpha-amylase activity was estimated at 11.7 and 9.5 units per ml of immobilized enzyme respectively for consecutive assays.

EXAMPLE III

Fungal Alpha-Amylase Immobilized on PEI Derivatized Granular Carbon

Fungal alpha-amylase was immobilized on derivatized carbon as described in example II. A 50 ml enzyme solution containing 0.1 gm of Sumizyme LP-8 fungal alpha-amylase (908 MMU/mg) adjusted to pH 7.0 was used to treat 5 ml of PEI-glutaraldehyde derivatized carbon. The activity of the immobilized preparation was measured as described in example II except that 1% Martrin-10 was used as the substrate. An activity of 5.2 and 5.5 units per ml of immobilized enzyme was obtained for consecutive assays. A unit of activity represents the amount of reducing group formed as measured by the ferricyanide method as a μ mole of glucose per minute.

EXAMPLE IV

Soy Beta-Amylase Immobilized on PEI-Glutaraldehyde Derivatized Granular Carbon The procedure described in example II was used to immobilize soy beta-amylase. A 50 ml enzyme solution (0.1 gm of a lyophilized sample, 182 units/gm) adjusted to pH 7.0 was used to treat 5 ml of the PEI-derivatized carbon. The immobilized enzyme preparation was assayed in the differential reactor using the conditions of the assay in example II. Consecutive assays of 2.6 and 2.4 units per ml of immobilized enzyme were obtained.

EXAMPLE V

Malt Amylase Immobilized on PEI-Glutaraldehyde Derivatized Granular Carbon

A 100 ml solution of malt amylase pH 7.0 (0.2 gm, Mylase-Wallerstain Lab) was used to treat 10 ml of PEI derivatized granular carbon by the procedure described in example II. The immobilized enzyme preparation was assayed in the differential reactor as described in example II using the 4% soluble starch for the substrate. An activity of 1.8 units per ml of immobilized enzyme was obtained. It should be noted that with many of the assays with granular carbon, substrate and product absorption may influence the actual rates as described by Cho, et al in *Biotechnol. Bioeng.*, 20:1651 (1978).

EXAMPLE VI

Wheat Beta-Amylase Immobilized on PEI-Glutaraldehyde Derivatized Granular Carbon A 0.2 gm quantity of wheat beta-amylase (lyophilized powder 140 MMU/mg) in 100 ml of DI water (pH 7.0) was used to treat 10 ml of PEI-glutaraldehyde derivatized carbon using the procedure described in example II. The activity of this preparation was estimated at 1.6 units per ml of immobilized enzyme using 4% soluble starch at pH 6.0 as the substrate in the differential reactor.

EXAMPLE VII

Pullulanase Immobilized on PEI-Glutaraldehyde Derivatized Granular Carbon

Pullulanase was immobilized in a manner similar to the procedure described in example VII by treating 10 ml of derivatized carbon with 100 ml of a pH 7.0 solution of pullulanase prepared by dissolving 0.2 gm of pullulanase (A.B.M. Chemicals Ltd., Sample K1000) in 100 ml of DI water. The activity of the enzyme preparation was estimated in the recirculation differential reactor at 50° C. using as substrate 0.2% pullulan in 0.02 M acetate buffer at pH 5.5. The extent of the digestion of pullulan was determined by the appearance of reducing groups. The reducing groups were estimated by the ferricyanide method using glucose as the reference. The production of reducing groups was plotted as a function of time and from the plot it was estimated that in 15 minutes of reaction, 15% of the pullulan was digested.

EXAMPLE VIII

Glucose Isomerase Immobilized on PEI-Glutaraldehyde Derivatized Granular Carbon Soluble glucose isomerase (GI) was obtained by treating washed cells of *Streptomyces olivaceus* with dilute detergent (0.1% Lubrol WX) and centrifuging to remove cell debris. A 100 ml quantity of soluble GI at pH 7.0 containing 2 units of activity per ml (unit=μmole of fructose/min.) was used to treat 10 ml of derivatized granular carbon as described in example II. The activity was estimated at 2.2 units per ml of immobilized enzyme in the differential reactor at 60° using a substrate containing 2 M glucose, 4.1 mM $MgSO_4.7H_2O$, 2.4 mM $NaHSO_3$ and 20 mM tris-maleate buffer pH 8.0. The amount of fructose formed was determined by the cysteine-$H_2SO_4$ method.

EXAMPLE IX

Fungal Lactase Immobilized on PEI-Glutaraldehyde Derivatized Granular Carbon Fungal lactase was immobilized on derivatized granular carbon by the procedure described in example II except that the 1% glutaraldehyde solution was buffered with 0.05 M borate at pH 9.0 and the enzyme solution was buffered with 0.05 M sodium phosphate at pH 7.0. Lactase solution (50 ml of 0.1 gm Miles Laboratories, Inc. fungal lactase, 14,280 FCCLU/gm) was used to treat 10 ml of PEI-derivatized carbon. The activity of the enzyme preparation was measured at 55° C. in the differential reactor using as substrate 0.15 M lactose in 0.02 M acetate buffer, pH 4.5. The breakdown of lactose was monitored by the amount of glucose formed as determined by the Glucostrate method. The activity was estimated at 38 units/ml of immobilized enzyme.

EXAMPLE X

Influence of the Molecular Size of PEI on Immobilizing Amyloglucosidase

In the preceeding examples, only 1 type of polyamine (Dow PEI-600, molecular weight range 40,000–60,000) was derivatized on granular carbon. In this example other molecular weight PEI's were used to determine the influence on enzyme binding. For this experiment, 50 ml solutions of 1% PEI-18 (1,800 MW), 2% PEI-200 (20,000–30,000 MW) and 1% PEI-600 (40,000–60,000 MW) were used to treat 10 ml of acid washed granular carbon. The procedure for derivatizing the carbon was similar to that described in example I except that the glutaraldehyde solution was buffered with 0.05 M borate at pH 9.0. Also the AG solution (2 ml Miles Diazyme L-100 diluted to 50 ml) was buffered with 0.05 M phosphate at pH 7.0.

The enzyme activity of the preparations were determined in the recirculation differential reactor as described in example I. The following table summarizes the activity.

| Derivatized Carbon | Activity (μ moles G/min./ml immob. enz.) |
|---|---|
| PEI-18 | 252 |
| PEI-200 | 232 |
| PEI-600 | 179 |

These results indicate that a wide molecular weight range of PEI can be used to immobilize enzyme, but the size of the polyamine molecule influences the amount of enzyme immobilized. The size of the PEI molecule to which the enzyme is bound may also influence the product profile obtained from liquefied starch digestion through a steric or mass transport phenomena.

EXAMPLE XI

Immobilization of AG on Betz 1180-Glutaraldehyde Derivatized Granular Carbon

In this example, another type of polyamine was used in place of polyethylenimine to immobilized AG. For this experiment, Betz 1180 was used as the polyamine. This polymer, which is marketed under the tradename Betz 1180 by Betz Laboratories, Inc., Trevose, Pa., is a water soluble cationic polymer obtained by the polymerization of an epihalohydrin with an alkylene polyamine. It has a molecular weight of less than 1 million, contains about 0.288 millimoles of amino groups per gram of solution (based on ninhydrin assay) and is marketed as a solution containing 30 weight percent solids, based on total solution weight. A more detailed description of this polymer and its preparation can be found in U.S. Pat. Nos. 3,915,904 and 3,953,330. The steps of polyamine absorption, amino group activation and enzyme immobilization were similar to that described in example I. The activity of the preparation was assayed as in example I at 236 units/ml of immobilized enzyme. This example demonstrates that polyamines other than polyethylenimine having pendant amine groups are suitable for use in this invention.

EXAMPLE XII

Immobilization of Glucose Isomerase on Double PEI-Derivatized Granular Carbon

The distance between the immobilized enzyme and the support, and the flexibility of the immobilized enzyme with respect to the support can be altered by reacting a polyamine in place of the enzyme to the absorbed derivatized polyamine, followed by derivatizing the new polyamine with glutaraldehyde for enzyme immobilization. This technique was tried by first absorbing a polyamine (PEI or Betz 1180) on acid washed granular carbon; secondly reacting the amino groups with glutaraldehyde; thirdly covalently binding a polyamine to the aldehyde group of glutaraldehyde; fourthly activating the amino group with glutaraldehyde and finally immobilizing the enzyme.

Experimental conditions were similar to those described in example XI for the polyamine and glutaraldehyde steps, except for the second polyamine treatment, in which the polyamine was made up in 0.05 M borate buffer at pH 9.0. Four samples were prepared using combinations of PEI-600 and Betz 1180. The enzyme used for immobilization was GI described in example VIII. The activities of the samples prepared are listed in the following table using the assay method described in example VIII.

| Sample | Activity ($\mu$ moles/fructose/ min./ml immob. enz.) |
|---|---|
| 1. PEI-GA-PEI | 4.4 |
| 2. PEI-GA-Betz | 4.3 |
| 3. Betz-GA-PEI | 4.8 |
| 4. Betz-GA-Betz | 4.5 |

The activity of all the preparations are more active than the GI immobilized in example VIII. It is possible that this method of immobilization may have increased the enzyme loading on the carbon particle, compared to the 2.2 units/ml of immobilized enzyme for the PEI-derivatized carbon used in example VIII.

EXAMPLE XIII

Preparative Technique of Immobilization of AG on Betz 1180 Derivatized Carbon

All of the previous examples of enzyme immobilization were done in a batch-wise fashion. This example gives the results of immobilizing AG on a 300 ml volume of support using a column technique.

Procedure (all steps at room temperature)
1. 300 ml of Darco 20/40 mesh activated granular carbon soaked in concentrated HCl for several hours.
2. Excess HCl decanted and the carbon washed with copious amounts of DI water.
3. Transferred carbon to 2.6×70 cm glass column and continued washing by perculating water through the bed until the effluent pH reached 3.9.
4. A 2 liter solution of polyamine (40 gm Betz 1180 diluted with DI water) was then perculated through the bed. After all the solution was passed through the bed, the solution was recycled upflow through the bed for 4 hours.
5. Excess polyamine was then washed from the carbon by washing with 4 liters of water (upflow).
6. 1.5 liters of 1% glutaraldehyde in 0.02 M borate buffer pH 9.0 was then perculated through the bed and then recycled upflow for about 16 hours.
7. Excess glutaraldehyde was then washed from the carbon with water in a manner similar to step 5.
8. 1.5 liters of enzyme solution (60 ml of Diazyme) in 0.2 M phosphate buffer pH 7.0 was perculated through the bed and then recycled upflow for about 5 hours.
9. The excess enzyme was then washed from the bed as described in step 5.
10. About 7 liters of 0.02 M citrate buffer pH 4.2 was then perculated through the bed over a period of about 18 hours, the pH of the effluent was then 4.2.
11. The immobilized enzyme preparation was removed from the column and stored in 0.02 M citrate buffer at pH 4.2.

The activity of the immobilized AG preparation estimated in the differential reactor as described in example I was 236 units per ml of immobilized enzyme. As indicated by this experiment, scale up to large quantities does not offer any inherent problems in immobilization.

EXAMPLE XIV

In this comparative example, additional experiments are described in which alumina and carbon are compared as supports for the immobilization of enzymes. Physical properties of the supports are summarized in the following table I. Several different parameters are compared.

In one experiment, amyloglucosidase (AG) was immobilized to the 2 support materials (alumina and carbon) using PEI/glutaraldehyde under identical conditions. Since one of the important properties of carbon is that it can be regenerated by a base-acid wash, both supports were subjected to a mild acid-base treatment prior to immobilization of the enzyme. For these experiments, the support material was mixed with the acid or base on a shaker for about 2 hours and then allowed to stand overnight. The reagent was then decanted, and the support was washed with large quantities of water prior to its treatment in the immobilization process. The results of these experiments are summarized in table 1a.

TABLE 1

Properties of Alumina and Granular Carbon

|  | Alumina[1] | Carbon[2] |
|---|---|---|
| Particle Size (mesh size) | 24/48 | 20/40 |
| Pore Volume (ml/gm) | .30 | .95 |
| Avg. Pore Diameter (A) | 45 | 200 |
| Surface Area (M$^2$/gm) | 210 | 600 |

[1] Activated alumina grade F1 from Alcoa, Pittsburgh, PA
[2] Activated granular carbon from Darco, Wilmington, DE

TABLE 1a

Influence of Acid and Alkaline Pretreatment of Alumina and Carbon in Binding Glucoamylase by the PEI-GA Method

| Treatment | Enzyme Presented To Support[a] (units) (ml support)$^{-1}$ | Enzyme Not Bound (%) | Enzyme Bound[b] (%) | Enzyme Bound[b] (units) (ml support)$^{-1}$ |
|---|---|---|---|---|
| Alumina | | | | |
| No treatment | 110 | 46 | 29 | 33.9 |
| HCl (.6 N) | 110 | 71 | 10 | 11.9 |
| NaOH (.25 N) | 110 | 55 | 26 | 29.5 |
| Carbon | | | | |
| No treatment | 110 | 0 | 70 | 81.0 |
| HCl (.6 N) | 110 | 0 | 79 | 91.1 |
| NaOH (.25 N) | 110 | 0 | 76 | 87.0 |

[a] Activity assayed by incubation at 50° C. for 60 minutes using as substrate 10% Maltrin-15 buffered at pH 4.2 with 20 mM citrate. A unit of activity represents the amount of enzyme that forms one $\mu$ mole of glucose per minute.
[b] Activity of immobilized enzyme was assayed under similar conditions as above by incubating the enzyme in flask placed in a shaker water bath. A unit of activity has the same definition as above [a].

The results summarized in table 1a show that with no prior treatment of the support, the carbon is more efficient in binding all the enzyme. Alumina is apparently more specific in its binding leaving approximately 50% of the enzyme unbound. Acid treatment of alumina apparently alters the structure of alumina in such a way that the binding capacity of this support is reduced as evidenced by the greater amount of activity remaining unbound and by the lower immobilized activity (units/ml). Treatment of alumina with a base, however, has little effect. Acid or base treatment of carbon can be seen to have essentially no influence on the binding characteristics of carbon. These results demonstrate the fundamental difference as to the relative binding properties and inertness of the support to a mild acid or base treatment.

Another series of experiments were conducted to evaluate the action profile of immobilized AG and its stability on both supports on digesting liquefied corn starch. The AG was immobilized on both supports withour prior acid or base treatment.

TABLE 2

Summary of Immobilization of Amyloglucosidase to Alumina and Carbon for Integral Column Study

| Support | Enzyme Presented To Support (units) (ml support)$^{-1}$ | Enzyme Unbound (%) | Enzyme Bound (%) | Enzyme Bound (units) (ml support)$^{-1}$ |
|---|---|---|---|---|
| Alumina | 106 | 45 | 24 | 25.7 |
| Carbon | 106 | 2 | 73 | 77.3 |

[1] 100 ml of alumina (28/48 mesh) and carbon (20/40 mesh) were used to immobilize amyloglucosidase (Diazyme L-100) using the PEI-GA process.

Table 2 summarizes the enzyme distribution during the immobilization process. Column reactors (100×1.5 cm glass jacket columns) were used to prepare columns containing equivalent amounts of each immobilized enzyme. For this experiment the columns consisted of a 10 ml bed of AG bound to carbon and a 30 ml bed of AG bound to alumina. Both columns were fed 25 DE (dextrose equivalent) unrefined alpha-amylase liquefied corn flour adjusted to 23% DS and containing 250 ppm SO$_2$ buffered with 5 mM citrate at pH 4.2. The substrate was perculated through the beds at a constant flow rate at about 10 ml per hour. The columns were maintained at a constant temperature by circulating 50° water through the column jacket. To determine the degree of digestion, the carbohydrate profile was obtained by subjecting the column effluent periodically to HPLC separation. The carbohydrate profiles of the digests by AG bound to the alumina and carbon are summarized in tables 3 and 4, respectively. Also in these tables the nominal reaction time and DE values are given. The nominal reaction times were longer for the AG bound to alumina because of its larger bed volume. The carbohydrate profiles are strikingly different even though both enzyme beds have identical units of activity (based on initial activity).

TABLE 3

Carbohydrate Profile of Digesting 25 DE pH 4.2 Liquefied Corn Starch by a 30 ml Bed of Amyloglucosidase Bound to Alumina in a 100 × 1.5 cm Glass Jacket Column at 50° C.

| Fr | Nominal Reaction Time (Hr) | Total Time (Hr) | DE[b] | Carbohydrate Profile[a] (%) DP$_1$ | DP$_2$ | DP$_3$ | DP$_4$ | DP$_5$ | DP$_6$ | >DP$_6$ |
|---|---|---|---|---|---|---|---|---|---|---|
| 1 | 3.29 | 17.75 | 52.2 | 28.7 | 20.5 | 15.0 | 4.0 | 4.0 | 2.8 | 24.9 |
| 2 | 2.94 | 41.75 | 61.5 | 38.4 | 26.7 | 8.0 | 1.6 | 1.4 | 1.7 | 22.2 |
| 3 | 3.02 | 65.5 | 66.5 | 45.0 | 27.6 | 3.5 | .8 | 1.1 | 1.6 | 20.4 |
| 4 | 2.99 | 89.5 | 68.8 | 48.8 | 26.2 | 2.0 | 1.1 | 1.3 | 1.5 | 19.0 |
| 5 | 2.97 | 113.25 | 69.8 | 50.7 | 24.9 | 1.7 | 1.0 | 1.4 | 1.7 | 18.7 |
| 6 | 2.97 | 137.25 | 70.3 | 52.0 | 23.8 | 1.4 | 1.2 | 1.3 | 1.5 | 18.7 |
| 7 | 3.23 | 162.25 | 72.6 | 56.0 | 21.4 | 1.0 | 1.2 | 1.3 | 1.5 | 17.6 |
| 8 | 3.12 | 186.0 | 74.6 | 61.1 | 16.0 | 1.4 | 1.4 | 1.2 | 1.3 | 17.6 |
| 9 | 2.87 | 208.75 | 73.4 | 60.0 | 15.5 | 1.3 | 1.0 | .9 | 1.0 | 20.3 |

TABLE 3-continued

Carbohydrate Profile of Digesting 25 DE pH 4.2 Liquefied Corn Starch by a 30 ml Bed of Amyloglucosidase Bound to Alumina in a 100 × 1.5 cm Glass Jacket Column at 50° C.

| Fr | Nominal Reaction Time (Hr) | Total Time (Hr) | DE[b] | Carbohydrate Profile[a] (%) | | | | | | |
|---|---|---|---|---|---|---|---|---|---|---|
| | | | | $DP_1$ | $DP_2$ | $DP_3$ | $DP_4$ | $DP_5$ | $DP_6$ | $>DP_6$ |
| 10 | 2.90 | 233.75 | 71.9 | 57.0 | 17.0 | 1.1 | .8 | .6 | .9 | 21.9 |
| 11 | 5.91 | 255.75 | 71.6 | 57.8 | 15.7 | 1.4 | 1.0 | .7 | 1.0 | 22.4 |
| 12 | — | — | | | | | | | | |
| 13 | 2.89 | 306.0 | 74.2 | 61.3 | 15.0 | 1.2 | .8 | .7 | .8 | 20.1 |
| 14 | 3.25 | 328.5 | 71.6 | 57.7 | 15.8 | 1.3 | 1.1 | .7 | 1.0 | 22.5 |
| 15 | 3.29 | 335.25 | 71.3 | 57.2 | 16.0 | 1.6 | 1.1 | .9 | 1.0 | 22.3 |
| 16 | 3.35 | 356.25 | 71.0 | 58.2 | 13.2 | 2.0 | 1.1 | 1.1 | 1.5 | 22.8 |
| 17 | 2.79 | 378.5 | 68.5 | 52.9 | 17.4 | 2.6 | 1.1 | 1.0 | .8 | 24.1 |
| 18 | 2.96 | 402.0 | 70.8 | 55.8 | 17.9 | 1.3 | .5 | .3 | .5 | 23.6 |
| Substrate | | | 25.1 | 3.7 | 9.3 | 15.8 | 5.4 | 24.1 | 14.2 | 27.6 |

[a]Carbohydrate profile obtained by HPLC using a Bio-Rad Aminex HPX-42 Column.
[b]DE was computed from the carbohydrate profile by using a program developed from known compositions.

TABLE 4

Carbohydrate Profile of Digesting 25 DE, pH 4.2 Liquefied Corn Starch by a 10 ml Bed of Amyloglucosidase Bound to Carbon in a 100 × 1.5 cm Glass Jacket Column at 50° C.

| Fr | Nominal Reaction Time (Hr) | Total Time (Hr) | DE[b] | Carbohydrate Profile[a] (%) | | | | | | |
|---|---|---|---|---|---|---|---|---|---|---|
| | | | | $DP_1$ | $DP_2$ | $DP_3$ | $DP_4$ | $DP_5$ | $DP_6$ | $>DP_6$ |
| 1 | .81 | 17.75 | 90.4 | 87.2 | 2.4 | 1.1 | 0 | 0 | 0 | 9.3 |
| 2 | .93 | 41.75 | 90.8 | 87.9 | 2.0 | 1.0 | 0 | 0 | 0 | 9.1 |
| 3 | 1.00 | 65.5 | 91.1 | 88.5 | 1.5 | 1.0 | 0 | 0 | 0 | 9.0 |
| 4 | .98 | 89.5 | 90.6 | 87.7 | 1.9 | .9 | 0 | 0 | 0 | 9.5 |
| 5 | .46 | 113.25 | 90.1 | 86.9 | 2.2 | 1.0 | 0 | 0 | 0 | 10.0 |
| 6 | .97 | 137.25 | 90.3 | 87.2 | 2.1 | .9 | 0 | 0 | 0 | 9.7 |
| 7 | 1.05 | 162.25 | 90.8 | 88.1 | 1.6 | 1.0 | 0 | 0 | 0 | 9.3 |
| 8 | 1.07 | 186.0 | 91.6 | 89.3 | 1.1 | .9 | 0 | 0 | 0 | 8.7 |
| 9 | 1.07 | 209.75 | 88.0 | 84.2 | 2.7 | .8 | 0 | 0 | 0 | 12.3 |
| 10 | .96 | 233.75 | 85.3 | 80.6 | 3.7 | .8 | 0 | 0 | 0 | 14.9 |
| 11 | .96 | 255.75 | 84.2 | 79.3 | 3.7 | .8 | 0 | 0 | 0 | 16.3 |
| 12 | .93 | 288.25 | 85.1 | 80.6 | 3.1 | .7 | 0 | 0 | 0 | 15.6 |
| 13 | 1.02 | 306.0 | 85.3 | 80.9 | 3.1 | .8 | 0 | 0 | 0 | 15.2 |
| 14 | .88 | 329.5 | 83.0 | 77.4 | 4.6 | .9 | 0 | 0 | 0 | 17.1 |
| 15 | 1.02 | 335.25 | 83.8 | 78.4 | 4.6 | .7 | 0 | 0 | 0 | 16.4 |
| 16 | .89 | 356.25 | 82.0 | 76.3 | 4.4 | .8 | 0 | 0 | 0 | 18.5 |
| 17 | 1.10 | 378.5 | 87.4 | 84.2 | 1.6 | .7 | 0 | 0 | 0 | 13.6 |
| 18 | .97 | 402.0 | 86.4 | 83.2 | 1.1 | .7 | 0 | 0 | 0 | 14.9 |
| Substrate | | | 25.1 | 3.7 | 9.3 | 15.8 | 5.4 | 24.1 | 14.2 | 27.6 |

[a]Carbohydrate profile obtained by HPLC, conditions given in Table 3.
[b]DE calculated by method given in Table 3.

From tables 3 and 4 it can be determined that AG immobilized to carbon digested the liquefied starch more completely as evidenced by the greater proportion of $DP_1$, low $DP_2$ and $DP_3$ oligosaccharides, and the complete digestion of the $DP_4$, $DP_5$ and $DP_6$, oligosaccharides. Also the $>DP_6$ fraction is substantially lower for the AG immobilized on carbon as compared to the AG immobilized to alumina. The higher levels of disaccharides ($DP_2$) and the intermediate oligosaccharides ($DP_3$ through $DP_6$) and the low level of glucose in the effluent from the AG-alumina column indicates an apparent loss in activity or the presence of some sort of mass transport phenomena causing the apparent loss of enzyme activity.

To quantitate the apparent loss of activity or some inability of AG bound to alumina to digest starch as effectively as AG bound to carbon, the activity can be expressed as $\mu$ moles of glucose formed/minute/ml of enzyme computed from the results given in tables 3 and 4. The activities are summarized in tables 5 and 6 for both immobilized enzymes. The activity results were also normalized to dimensionless activity by dividing the observed activity from the column digests by the initial velocity activity obtained by assaying the immobilized enzyme in the shaker bath using Maltrin 15 as a substrate. The dimensionless activity of AG bound to carbon is almost twice the dimensionless activity of AG bound to alumina.

TABLE 5

Expressed Activity of Glucoamylase Immobilized to Alumina (Table 3) on Digesting 25 DE Liquified Corn Starch

| Fr | Fraction Time (Hr) | Total Time (Hr) | Flow Rate (ml/Hr) | Nominal Reaction Time (Hr) | Activity $\left(\frac{\mu \text{ mole G}}{(\text{min}) (\text{ml enz})}\right)$ | Normalized[a] Activity | % DP$_1$ |
|---|---|---|---|---|---|---|---|
| 1 | 17.75 | 17.75 | 9.11 | 3.29 | 1.78 | .069 | 28.7 |
| 2 | 24.0 | 41.75 | 10.20 | 2.94 | 2.78 | .109 | 38.4 |
| 3 | 23.75 | 65.5 | 9.98 | 3.01 | 3.18 | .124 | 45.0 |
| 4 | 24.0 | 89.5 | 10.04 | 2.99 | 3.44 | .134 | 48.8 |
| 5 | 23.75 | 113.25 | 10.09 | 2.97 | 3.67 | .143 | 50.7 |
| 6 | 24.0 | 137.25 | 10.10 | 2.97 | 3.77 | .147 | 52.0 |
| 7 | 25.0 | 162.25 | 9.30 | 3.23 | 3.57 | .139 | 56.0 |
| 8 | 23.75 | 186.0 | 9.63 | 3.12 | 3.69 | .144 | 61.1 |
| 9 | 23.75 | 209.75 | 10.45 | 2.87 | 3.88 | .151 | 60.0 |
| 10 | 24.0 | 233.75 | 10.34 | 2.90 | 4.05 | .158 | 57.6 |
| 11 | 22.0 | 255.75 | 5.08 | 5.91 | 2.05 | .080 | 57.8 |
| 12 | 32.5 | 288.25 | — | — | — | — | — |
| 13 | 17.75 | 306.0 | 10.37 | 2.89 | 4.97 | .193 | 61.3 |
| 14 | 23.5 | 329.5 | 9.24 | 3.25 | 4.15 | .161 | 57.7 |
| 15 | 5.75 | 335.25 | 9.13 | 3.29 | 3.84 | .149 | 57.2 |
| 16 | 21.0 | 356.25 | 8.46 | 3.35 | 3.86 | .150 | 58.2 |
| 17 | 22.25 | 378.5 | 10.76 | 2.79 | 4.23 | .165 | 52.9 |
| 18 | 23.5 | 402.0 | 10.12 | 2.96 | 4.08 | .159 | 55.8 |
| Substrate | | | | | | | 3.7 |

[a]Normalized activity is dimensionless activity derived by dividing activity obtained from a plug flow reactor by the initial velocity activity (25.7 units/ml).

TABLE 6

Expressed Activity of Amyloglucosidase Immobilized to Carbon (Table 4) on Digesting 25 DE Liquified Corn Starch

| Fr | Fraction Time (Hr) | Total Time (Hr) | Flow Rate (ml/Hr) | Nominal Reaction Time (Hr) | Activity $\left(\frac{\mu \text{ mole G}}{(\text{min}) (\text{ml enz})}\right)$ | Normalized[a] Activity | % DP$_1$ |
|---|---|---|---|---|---|---|---|
| 1 | 17.75 | 17.75 | 12.27 | 4.81 | 23.69 | .306 | 87.2 |
| 2 | 24.0 | 41.75 | 10.70 | .93 | 21.34 | .276 | 87.9 |
| 3 | 23.75 | 65.5 | 10.01 | 1.00 | 20.10 | .260 | 88.5 |
| 4 | 24.0 | 89.5 | 10.16 | .98 | 20.15 | .261 | 87.7 |
| 5 | 23.75 | 113.25 | 10.37 | .96 | 20.59 | .266 | 86.9 |
| 6 | 24.0 | 137.25 | 10.30 | .97 | 20.41 | .264 | 87.2 |
| 7 | 25.0 | 162.25 | 9.50 | 1.05 | 18.68 | .242 | 88.1 |
| 8 | 23.75 | 186.0 | 9.36 | 1.07 | 16.50 | .213 | 89.3 |
| 9 | 23.75 | 209.75 | 9.37 | 1.07 | 15.39 | .199 | 84.2 |
| 10 | 24.0 | 233.75 | 10.43 | .96 | 18.59 | .240 | 80.6 |
| 11 | 22.0 | 255.75 | 10.47 | .96 | 18.84 | .244 | 79.3 |
| 12 | 32.5 | 288.25 | 10.72 | .93 | 19.82 | .256 | 80.6 |
| 13 | 17.75 | 306.0 | 9.78 | 1.02 | 18.31 | .237 | 77.4 |
| 14 | 23.5 | 329.5 | 11.31 | .88 | 20.08 | .260 | 77.4 |
| 15 | 5.75 | 335.25 | 9.85 | 1.02 | 17.61 | .228 | 78.3 |
| 16 | 21.0 | 356.25 | 11.26 | .89 | 18.71 | .242 | 76.3 |
| 17 | 22.25 | 378.5 | 9.10 | 1.10 | 17.85 | .231 | 84.2 |
| 18 | 23.5 | 402.0 | 10.26 | .97 | 19.76 | .256 | 82.3 |
| Substrate | | | | | | | 3.7 |

[a]See table 5, initial velocity activity of glucoamylase bound to carbon is 77.3 units/ml.

Comparing the dimensionless activity from the results of both immobilized forms of AG is a relatively crude estimate since the conversion of both columns were not similar. However, the wide variation in the dimensionless activity indicates a fundamental difference of the immobilized form of AG in digesting Maltrin 15 (15 DE) and to convert a liquefied corn starch (25 DE). The conclusion one can draw from these results is that AG bound to carbon can digest small chained oligosaccharide to glucose more readily than AG bound to alumina. This suggests that the AG bound to carbon is relatively more free than the AG bound to alumina.

Both forms of immobilized AG appear to be quite stable as indicated by table I. It is interesting to note that initially the AG bound to carbon lost some apparent activity up to about 50 hours of operation and then reached a steady state through 400 hours of operation. AG bound to alumina resulted in an apparent increase in activity during the initial 50 hours of operation suggesting some sort of mass transport resistance. The data in table 1 indicate that after an apparent steady state, AG bound to alumina was about 20% of that expressed by AG bound to carbon.

From these experiments it has been demonstrated that under identical conditions, carbon binds more AG (77.3 units/ml) than alumina (25.7 units/ml). AG bound to carbon appears to be less affected by the influence of mass transfer resistance than AG bound to alumina since AG bound to carbon digests liquefied corn starch more completely than AG bound to alumina. It has also been demonstrated that carbon is stable to both acid and base treatment, whereas alumina is stable to base treatment but liable to acid treatment. The stability of a support to both acid and base is necessary for the regeneration of the support to be reused for enzyme immobilization. Together these results clearly illustrate that carbon and alumina, when used as a support for immobilizing enzymes by the PEI-glutaraldehyde method, are quite different.

What is claimed is:

1. A method of preparing an immobilized enzyme conjugate which comprises the steps of:
   (a) contacting porous, granular, activated carbon having a particle size of from 12 to 40 mesh on the U.S. sieve series, pore dimensions of from 35 to 1,000 Å in radius and a surface area of from 200 to 600 m$^2$/gm with a solution of a polyamine compound having pendant amine groups to cause the polyamine to attach itself to the carbon both by absorption to its surface and by entrapment in the pores thereof;
   (b) removing the water and any unattached polyamine dispersed therein from contact with the carbon and contacting it with an aqueous solution of an amine reactive material which is a multifunctional aldehyde, a multifunctional organic halide, a multifunctional anhydride, a multifunctional azo compound, a multifunctional isothiocyanate or a multifunctional isocyanate to cause one of the reactive groups to react with the pendant amine groups and leave an amine reactive moiety available for further reaction;
   (c) removing the water and any unreactive amine reactive material dissolved therein from contact with the carbon and contacting the carbon with an aqueous solution of the enzyme to be immobilized to cause the amine groups of the enzyme to react with the unreacted amine reactive moiety by the formation of covalent bonds therebetween to thereby immobilize the enzyme.

2. The method of claim 1 wherein the polyamine is selected from the group of polyethylenediamine, a polyethylenimine, polyhexamethylene-diamine, polymethylenedicyclohexylamine, polymethylenedianiline, polytetraethylenepentamine, and polyphenylenediamine.

3. The method of claim 2 wherein the polyethylenimine is polydiethylenetriamine, polytriethylenetetramine, polypentaethylene-hexamine or polyhexamethylenediamine.

4. The method of claim 1 wherein the polyamine is a copolymer of an epihalohydrin and an alkylene polyamine.

5. The method of claim 1 wherein the polyamine has a molecular weight range of from 500 to 100,000.

6. The method of claim 1 wherein the amine reactive material is bis-diazobenzidine-2,2'-disulfonic acid; 4,4'-difluoro-3,3'-dinitrodiphenylsulfone; diphenyl-4,4'-dithiocyanate-2,2'-disulfonic acid; 3-methoxydiphenylmethane-4,4'-diisocyanate; toluene-2-isocyanate-4-isothiocyanate, toluene-2,4-diisothiocyanate; diazobenzidine; diazobenzidine-3,3'-dianisidine; N,N'-hexamethylene bisiodoacetamide; hexamethylene diisocyanate; cyanuric chloride or 1,5-difluoro-2,4-dinitrobenzene.

7. The method of claim 1 or 2 wherein the amine reactive material is glutaraldehyde.

8. The method of claim 1 wherein the enzyme is glucoamylase.

9. An immobilized enzyme conjugate comprising porous, granular, activated carbon having a particle size of from 12 to 40 mesh on the U.S. sieve series, pore dimensions of from 35 to 1,000 Å in radius and a surface area of from 200 to 600 m$^2$/gm as a support having attached thereto the reaction product of a polyamine compound having pendant amine groups, an amine reactive material which is a multifunctional aldehyde, a multifunctional organic halide, a multifunctional anhydride, a multifunctional azo compound, a multifunctional isothiocyanate or a multifunctional isocyanate whose unreacted amine reactive groups have been reacted with free amine groups of the enzyme to bind it thereto.

10. The conjugate of claim 9 wherein the polyamine is selected from the group of polyethylenediamine, a polyethylenimine, polyhexamethylenediamine, polymethylenedicyclohexylamine, polymethylenedianiline, polytetraethylenepentamine and polyphenylenediamine.

11. The conjugate of claim 10 wherein the polyethylenimine is polydiethylenetriamine, polytriethylenetetramine, polypentaethylene-hexamine or polyhexamethylenediamine.

12. The conjugate of claim 9 wherein the polyamine is a copolymer of an epihalohydrin and an alkylene polyamine.

13. The conjugate of claim 9 wherein the polyamine has a molecular weight of from 500 to 100,000.

14. The conjugate of claim 9 wherein the amine reactive material is bis-diazobenzidine-2,2'-disulfonic acid; 4,4'-difluoro-3,3'-dinitrodiphenylsulfone; diphenyl-4,4'-dithiocyanate-2,2'-disulfonic acid; 3-methoxydiphenylmethane-4,4'-diisocyanate; toluene-2-isocyanate-4-isothiocyanate, toluene-2,4-diisothiocyanate; diazobenzidine; diazobenzidine-3,3'-dianisidine; N,N'-hexamethylene bisiodoacetamide; hexamethylene diisocyanate; cyanuric chloride or 1,5-difluoro-2,4-dinitrobenzene.

15. The conjugate of claim 9 or 10 wherein the amine reactive material is glutaraldehyde.

16. The conjugate of claim 9 wherein the enzyme is glucoamylase.

17. A method of preparing an immobilized glucoamylase conjugate, and saccharifying starch, which comprises the steps of:
   (a) contacting porous, granular, activated carbon having a pore volume of about 0.95 ml/gm, an average pore diameter of about 200 angstroms and an average surface area of about 600 m$^2$/gm with a solution of a polyamine compound having pendant amine groups to cause the polyamine to attach itself to the carbon both by absorption to the surface and by entrapment in the pores thereof;
   (b) removing the water and any unattached polyamine dispersed therein from contact with the carbon and contacting it with an aqueous solution of an amine reactive material which is a multifunctional aldehyde, a multifunctional organic halide, a multifunctional anhydride, a multifunctional azo compound, a multifunctional isothiocyanate or a multifunctional isocyanate to cause one of the amine reactive groups to react with the pendant amine groups and leave an amine reactive moiety available for further reaction;
   (c) removing the water and any unreacted amine reactive material dissolved therein from contact with the carbon and contacting the carbon with an aqueous solution of the enzyme to be immobilized to cause the amine groups of the glucoamylase to react with the unreacted amine reactive moiety by the formation of covalent bonds therebetween to thereby immobilize the glucoamylase; and (d) contacting a bed of the immobilized glucoamylase with liquid starch to thereby accomplish the saccharification of the starch.

18. The method of claim 17 wherein after sufficient starch has been saccharified to wholly or partially inactive the glucoamylase, the bed of immobilized glucoamylase is washed with dilute hydrochloric acid to thereby restore the granular, activated carbon for reuse.

* * * * *